United States Patent
Dragan et al.

[11] Patent Number: 6,059,570
[45] Date of Patent: May 9, 2000

[54] DENTAL CONTAINER TYPE APPLICATOR

[75] Inventors: William B. Dragan, Easton; John J. Discko, Jr., Trumbull, both of Conn.

[73] Assignee: Centrix, Inc., Shelton, Conn.

[21] Appl. No.: 09/121,363

[22] Filed: Jul. 23, 1998

[51] Int. Cl.$^7$ .............................. A61G 17/02; A61C 5/04
[52] U.S. Cl. .............................. 433/80; 433/90; 401/129; 401/183
[58] Field of Search .......................... 433/80, 89, 90 OR; 604/2, 310, 311; 401/129, 183, 184, 185

[56] References Cited

U.S. PATENT DOCUMENTS

| | | | |
|---|---|---|---|
| D. 224,655 | 8/1972 | Dragan | D24/99 |
| D. 292,825 | 11/1987 | Dragan | D24/16 |
| D. 315,956 | 4/1991 | Dragan | D24/14 |
| D. 359,119 | 6/1995 | Dragan et al. | D24/114 |
| 3,581,399 | 6/1971 | Dragan | 433/90 |
| 3,900,954 | 8/1975 | Dragan | 433/90 |
| 4,198,756 | 4/1980 | Dragan | 433/90 |
| 4,211,247 | 7/1980 | Morganroth | 132/270 |
| 4,222,677 | 9/1980 | Cervantes | 401/129 |
| 4,256,409 | 3/1981 | Manley | 401/183 |
| 4,330,280 | 5/1982 | Dougherty et al. | 433/90 |
| 4,391,590 | 7/1983 | Dougherty | 433/90 |
| 4,578,055 | 3/1986 | Fischer | 604/2 |
| 4,619,613 | 10/1986 | Dragan | 433/90 |
| 4,963,093 | 10/1990 | Dragan | 433/90 |
| 4,969,816 | 11/1990 | Drumm | 433/90 |
| 4,997,371 | 3/1991 | Fischer | 433/90 |
| 5,001,803 | 3/1991 | Discko, Jr. | 15/167.1 |
| 5,052,927 | 10/1991 | Discko, Jr. | 433/90 |
| 5,083,921 | 1/1992 | Dragan | 433/90 |
| 5,122,057 | 6/1992 | Discko, Jr. | 433/90 |
| 5,129,825 | 7/1992 | Discko, Jr. | 433/90 |
| 5,150,495 | 9/1992 | Discko, Jr. | 15/167.1 |
| 5,165,890 | 11/1992 | Discko, Jr. | 433/90 |
| 5,172,807 | 12/1992 | Dragan et al. | 206/219 |
| 5,246,371 | 9/1993 | Fischer | 433/90 |
| 5,267,859 | 12/1993 | Discko, Jr. | 433/90 |
| 5,286,257 | 2/1994 | Fischer | 433/90 |
| 5,324,273 | 6/1994 | Discko, Jr. | 604/240 |
| 5,336,088 | 8/1994 | Discko, Jr. | 433/90 |
| 5,460,523 | 10/1995 | Schulman | 433/90 |
| 5,570,966 | 11/1996 | Phelan | 401/186 |
| 5,707,234 | 1/1998 | Bender | 433/90 |
| 5,755,572 | 5/1998 | Bab et al. | 433/216 |
| 5,816,804 | 10/1998 | Fischer | 433/90 |

FOREIGN PATENT DOCUMENTS

| 39 37 030 C2 | 11/1995 | Germany . |
|---|---|---|

*Primary Examiner*—John J. Wilson
*Attorney, Agent, or Firm*—Fattibene & Fattibene; Arthur T. Fattibene; Paul A. Fattibene

[57] ABSTRACT

A dental container type applicator in the form of a capsule, dental tip or squeeze bottle having a body portion terminating in a discharge nozzle having a discharge orifice upon which minute fibers or flocking is adhered about the external surface of the discharge nozzle in the vicinity of the discharge orifice to permit the user to spread, burnish or distribute the dental material onto a tooth as it is being expressed from the dental capsule, tip or squeeze bottle without obstructing the flow of dental material therefrom as the dental material is being expressed.

12 Claims, 3 Drawing Sheets

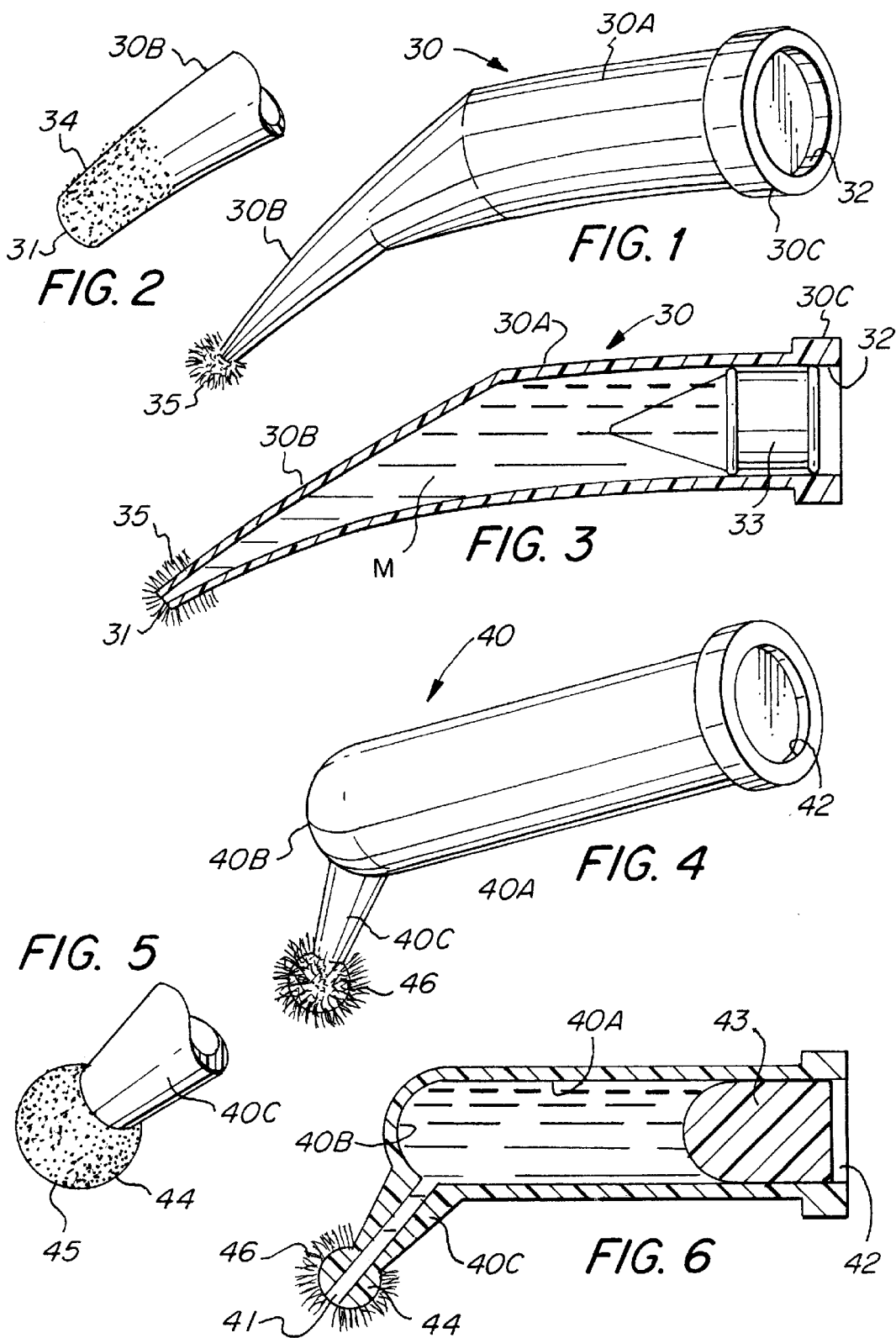

DENTAL CONTAINER TYPE APPLICATOR

FIELD OF THE INVENTION

This invention is generally directed to dental container type applicators, and more specifically to container type applicators in the form of a dental capsule, tip or squeeze bottle having the discharge end thereof coated with flocking to more effectively and precisely apply, distribute, spread or place a fluid dental material at the site of a given procedure as the material is being directly dispensed from the capsule or tip.

BACKGROUND OF THE INVENTION

The application and dispensing of various dental materials directly to a tooth surface during a tooth restoration or cosmetic procedure has been known for some time. The application and placement of dental materials directly to the site of the restoration or procedure using a syringe technique is disclosed in U.S. Pat. Nos. 3,581,399; 3,900,954; 4,198,756 and Design Pat. No. 224,655. These patents disclose the syringing technique of utilizing a unit dose capsule formed of a suitable plastic material having a reservoir for containing a predetermined amount of dental material having a discharge end or nozzle through which the dental material is extruded by the displacement of a piston sealing the open end of the capsule.

Subsequently, others attempted to duplicate the technique of placing dental materials to the site of the procedure, using only slightly modified constructions, such as evidenced by U.S. Pat. Nos. 4,330,280; 4,391,590; and 5,707,234. These later issued patents disclose a capsule design similar to the earlier issued Dragan patents, but differing therefrom in that the closed end of the capsule was provided with a known hemispherical shape.

As the syringing technique and the use of unit dose capsules for dispensing dental material gained recognition as a preferred method of placing dental material within the dental profession, various other capsule configurations have been made as evidenced by U.S. Pat. No. 4,619,613; DES Pat. No. 292,825; 4,963,093; 4,969,816; DES Pat. No. 315,956; U.S. Pat. No. 5,052,927; 5,083,921; 5,122,057; 5,129,825; 5,165,890; 5,172,807; 5,267,859; 5,324,273; 5,336,088, and DES Pat. No. 359,119. Reference is also made to the capsule construction of U.S. Pat. No. 5,460,523 assigned to Jeneric/Pentron, which appears to be a mere variation of the capsules of the previously noted patented constructions.

The foregoing noted patented constructions are essentially directed to a capsule body having a reservoir for containing a predetermined amount of dental material having a discharge nozzle at one end and a flange circumscribing an opening at the other end, and through which the material is loaded into the capsule, after which the opening is sealed by a displaceable piston for expressing the material in the reservoir through the discharge nozzle as the piston is displaced by a syringe applicator.

A further variation of dental capsules is evidenced in U.S. Pat. No. 4,578,055; 4,997,371; and 5,246,371. These patents are directed to a dental tip or capsules having a body portion terminating in a discharge nozzle in which a strand of bristles are slidably secured within the discharge nozzle so that the bristles may be pushed into and out of the discharge nozzle for applying a dental material to either a small or large area accordingly. It has been noted that the strand of bristles located internally of the discharge opening constitute an obstruction to the flow of dental material therethrough. A further limitation noted with the constructions of the latter identified patents is that the bristles are unidirectional so that the dental material can be applied only at the tip end of the bristles. Also, the insertion of a stand of bristles into the relatively small orifice of the discharge opening requires a tedious, time consuming and a relatively expensive procedure.

Various types of brush applicators for applying a dental material to a tooth are also known, as evidenced by U.S. Pat. Nos. 5,001,803; 5,150,495 and German Patent DE 3937030. However, such brush type applicators have the disadvantage that the brush must be repeatedly dipped into the dental material being applied, which may constitute a source of cross contamination and/or waste of dental material.

SUMMARY OF THE INVENTION

An object of this invention is to provide a dental capsule or tip having a discharge nozzle through which a dental material is applied directly to a tooth, and which has bonded to the exterior surface of the discharge nozzle adjacent the discharge opening a plurality of relatively small fibers projecting outwardly therefrom.

Another object is to provide a dental capsule or dental tip having minute fibers coated upon or adhered to the exterior surface of the discharge nozzle adjacent the discharge opening whereby the dental material can be applied, spread or burnished onto the tooth as the dental material is being expressed through the dental capsule or tip.

Another object is to provide a dental capsule or dental tip having a discharge nozzle formed with minute brushlike filaments about the exterior surface thereof to facilitate the placement of the material onto the tooth without obstructing the flow of dental material being expressed through the discharge opening of the dental capsule or tip.

Another object is to provide an improved dental capsule or tip construction to facilitate the spreading or burnishing the dental material onto a tooth as the material is being expressed from the capsule or tip.

Another object of the invention is to provide a dental capsule or tip having minute fibers bonded adjacent the discharge opening whereby the user can exert pressure onto the surface of the tooth without causing the fibers to "splay" or block the flow of dental material being expressed from the dental capsule or tip.

Another object of this invention is to provide an improved dental capsule or tip construction whereby the material can be spread or burnished onto a tooth that is relatively simple in construction, can be easily manufactured, and which is positive in operation.

The foregoing objects and other features and advantages are attained by a dental capsule or tip, adapted to contain a predetermined amount of dental material, which has a discharge nozzle at one end and an opening on the opposite end for receiving the material to be dispensed. In accordance with this invention, the discharge nozzle adjacent the orifice opening has bonded thereto a plurality of minute fibers projecting generally in a radially outwardly direction in a 360° direction. The arrangement is such that the fibers are bonded or adhered to the outer surface of the discharge nozzle so as to not obstruct the flow of material through the discharge nozzle as dental material is being expressed. The fibers bonded to the discharge end of the dental capsules or tips permit the user to exert a pressure on the tooth to spread or burnish the material onto the tooth as the material is being expressed, without obstructing the flow of material so as to greatly facilitate the application of a dental material to a tooth in a more simple and expedient manner than heretofore possible.

3

IN THE DRAWINGS

FIG. 1 is a perspective view of a dental capsule embodying the invention.

FIG. 2 is a fragmentary view of the discharge end of a capsule illustrating an intermediate showing.

FIG. 3 is a sectional side view of a capsule embodying the invention.

FIG. 4 is a perspective view of a modified embodiment of the invention.

FIG. 5 is a fragmentary detail view of the discharge end of FIG. 4.

FIG. 6 is a sectional side view of FIG. 4.

DETAILED DESCRIPTION

Figure 7:
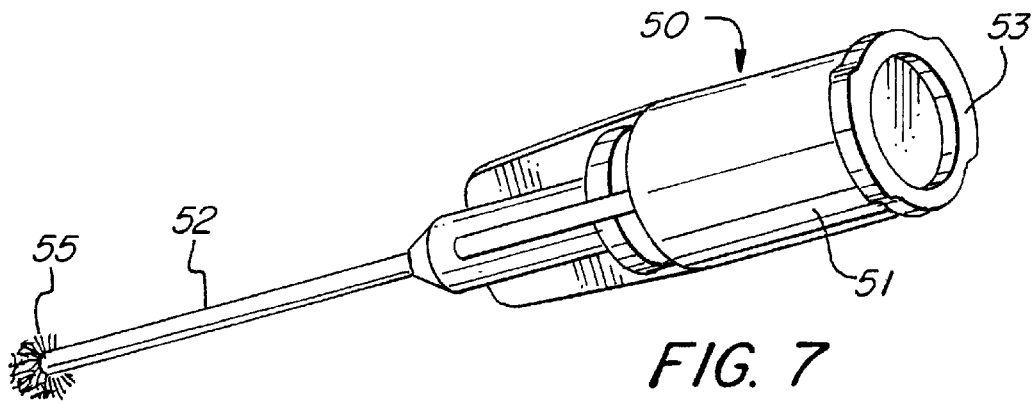
FIG. 7 is a perspective view of another modified form of the invention.

This invention is directed to a dental container type applicator whereby the flowable dental material can be readily expressed therefrom directly onto a tooth so that the flowable material can be readily spread, painted or burnished onto the tooth as the flowable dental material is being expressed therefrom. The container applicator of this invention may be in the form of a capsule, a dental tip or nozzle, or a squeeze type bottle having a discharge nozzle, as will be herein described.

Referring to the drawings, there is illustrated in FIG. 1 a dental container embodying the invention in the form of a dental capsule. Capsule, as defined herein, comprises a dental capsule having a body portion defining a reservoir for containing a predetermined amount of dental material and from which the dental material is extruded, as for example by a displaceable piston.

As shown in FIG. 1, the dental capsule 30, formed of a suitable plastic material, includes a generally cylindrical body portion 30A defining a reservoir for containing a predetermined amount of a fluid dental material M, e.g. sealants, cements, bonding agents, flowable composites and/ or like dental materials having a generally low viscosity. In the illustrated embodiment, one end of the capsule 30 tapers to define a discharge nozzle 30B which terminates at a discharge orifice or opening 31, through which the material disposed within the body portion 30A is dispensed. The other end of the capsule 30 is provided with a full opening 32 circumscribed by a laterally outwardly extending flange 30C. A piston 33, which is freely displaceable within the body portion 30A, seals opening 32.

In accordance with this invention, the external surface of the discharge nozzle adjacent the orifice or opening 31 is coated with a layer of suitable adhesive or bonding agent 34, to which a plurality of minute fibers 35 are adhered so as to extend in a generally radially outwardly direction about the entire circumference of the nozzle 30B in the vicinity of the orifice or opening 31. The fibers 35 may be in the form of a flocking type fiber which can be applied to the discharge end of the capsule 30 by an electrostatic process in which the fibers 35 are oppositely charged to that of the capsule, whereby the fibers 35 are attracted to the discharge end and are bonded thereto by the layer of adhesive 34.

With the fibers 35 bonded to the tip end of the nozzle 30B, it will be noted that the radially outwardly extending fibers 35 adjacent the orifice 31 function as a miniature brush by which the dentist may burnish or spread the dental material M onto a tooth as the material M is being extruded directly from the capsule 30 to a tooth. The construction described enables the dentist to precisely place and spread the dental material in a manner not feasible by capsule construction heretofore known; and without imposing any obstruction to the flow of material M being extruded from the capsule 30.

Generally, the capsule 30 described may be preloaded with a predetermined amount of material, i.e. enough for a single application or unit dose. It will also be understood that the capsule 30 described herein may be used with a syringe of the type disclosed in U.S. Pat. No. 3,581,399; 4,198,756 and other like syringes which are now a standard within the dental profession.

FIGS. 4 to 6 illustrate a slightly modified form of the invention. In this form of the invention, the capsule 40 comprises an elongated cylindrical body portion 40A defining a reservoir for containing a supply of dental material. In this form of the invention, the capsule 40 is closed at one end by a hemispherical end wall 40B. Connected adjacent end wall 40B and extending at an angle relative to the central axis of the body portion 40A is a discharge nozzle 40C which is disposed in communication with the reservoir. The nozzle 40C terminates at a discharge orifice 41. The other end of the capsule 40 is provided with a full open end 42 and a piston 43 seals the opening 42. Displacement of the piston 43 within the reservoir effects the extrusion of the dental material through the discharge orifice 41 of nozzle 40C.

In this form of the invention, the tip end of the nozzle 40C is formed in the configuration of a small sphere 44. A layer 45 of suitable adhesive or bonding material is applied to the spherical or ball tip 44, as best seen in FIG. 5, and to which a plurality of minute fibers or flocking 46 is subsequently adhered as best seen in FIGS. 4 and 6. In this form of the invention, it will be noted that the minute fibers 46 project generally radially outwardly of ball tip 44 over the entire surface of the ball tip 44 in every direction. In use and application, the capsule construction of FIGS. 4 to 6 is similar to the embodiment of FIGS. 1 to 3, except that the flocked ball tip 44, as disclosed in FIGS. 4 to 6, has a greater surface area for distributing or spreading the material, as the material can be distributed about the entire surface of the ball tip 44.

Figure 8:
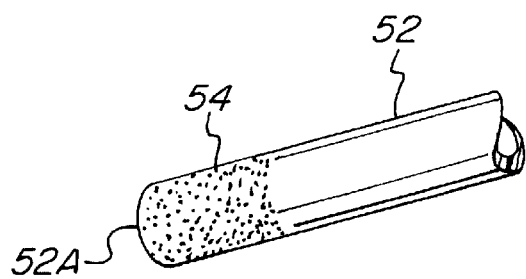
FIG. 8 is a fragmentary view of a detail of construction relating to the embodiment of FIG. 7.
Figure 9:
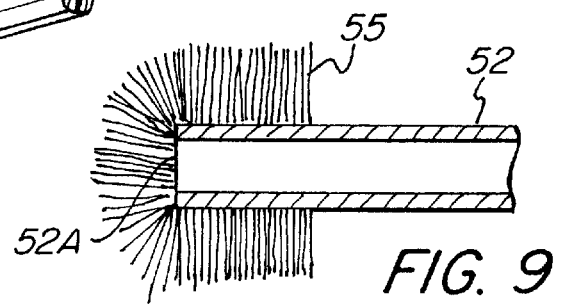
FIG. 9 is a fragmentary detail sectional view of the discharge end of the embodiment of FIG. 7.

FIGS. 7 to 9 are directed to another modified form of the invention. FIGS. 7 to 9 illustrate a dental tip 50. A dental tip, as herein used, is defined as a component that is detachably connected to the end of a syringe or other container containing a quantity of material wherein the tip 50 functions primarily as a nozzle for directing the material from the syringe or container to the site of a tooth being worked on.

The dental tip 50, as shown in FIG. 7, comprises a body portion 51 having a needle like canula 52 connected to one end of the body 51 and a Luhr locking flange 53 at the other end of the body. The Luhr locking flange 53 is constructed so as to releasably mate or lock tip 50 to the end of a syringe or other container defining the reservoir for the dental material (not shown) by effecting a half turn of the tip 50 relative to the syringe. The needle canula 52 is generally formed of metal, but can also be made of a suitable plastic. The canula 52, when formed of metal, is preferably formed of a ductile metal which can be bent so that the discharge end or orifice 52A may be disposed at an angle relative to the longitudinal axis of the tip body 51. The needle like canula 52 may be mounted or connected to the end of the body 51 in a manner described in U.S. Pat. No. 5,052,927, which is incorporated herein by reference.

As hereinbefore described, a layer 54 of adhesive or bonding material is coated onto the discharge end of the needle cannula 52, to which the fibers or flocking fibers 55 are adhered. In use, the dentist, in dispensing the dental material through the tip 50, can effectively brush, spread or burnish the dental material, as desired, by the fibrous coated canula.

Figure 10:
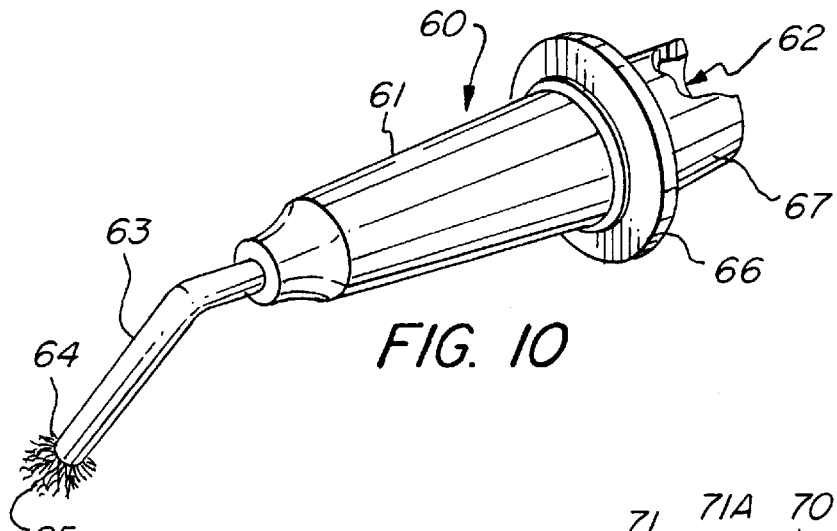
FIG. 10 is a sectional view of a modified form of the invention.

FIG. 10 is a slightly modified dental tip 60. Dental tip 60 includes a body portion 61 provided with an opening 62 at one end and a discharge needle like cannula 63 projecting outwardly at the other end. The needle canula 63 is formed of a suitable ductile metallic material which can be readily bent to a desired angle as shown. The tip end of the canula 63 adjacent the discharge orifice 64 is coated with fibers or flocking 65 as hereinbefore described. Intermediate the opposed ends of the body portion 61, there is provided a circumscribing flange 66. The portion 67 between flange 66 and the full opening 62 defines a nipple by which the tip 60 may be frictionally secured to the end of a syringe or other suitable container from which a dental material may be expressed.

Figure 11:
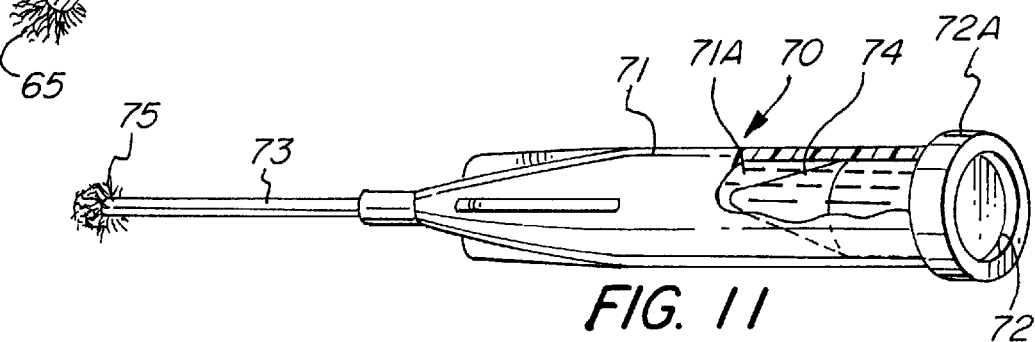
FIG. 11 is a sectional view of yet another modified form of the invention.

FIG. 11 illustrates another modified form of the invention in the form of a dental capsule 70 having an elongated cylindrical body portion 71 which is opened at one end 72 and has an elongated needle like canula 73 connected to the other end, similar to that described in U.S. Pat. No. 5,052,927. An outwardly extending flange 72A circumscribes the open end 72. A piston 74 seals the open end 72. As hereinbefore described, the canula 73 may be bent to any desired angle, and coated with fibers or flocking 75 adjacent the discharge orifice of the needle cannula. The dental material to be dispensed is confined within the reservoir 71A defined within body 71.

Figure 12:
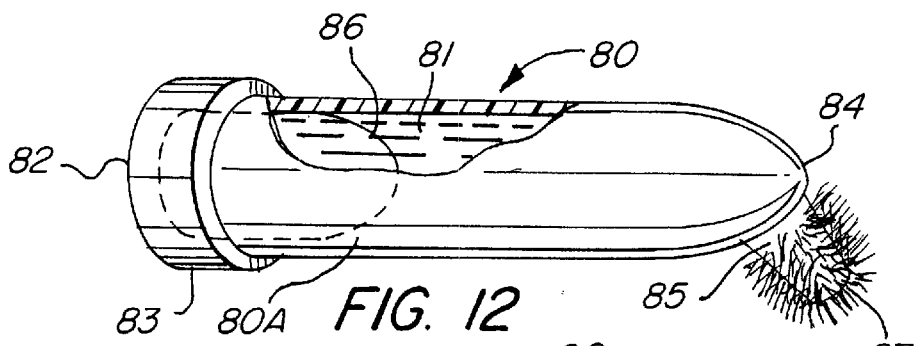
FIG. 12 is a perspective view of another form of the invention having parts broken away.

FIG. 12 is directed to a dental capsule 80 similar in construction to that disclosed in U.S. Pat. No. 4,963,093 and embodying the invention described herein. Dental capsule 80 comprises an elongated cylindrical or tubular body 80A defining a reservoir 81 for containing a predetermined amount of dental material, e.g. sealant, cement, low viscosity composite material and the like. One end of the body 80A is provided with an opening 82 circumscribed by a radially extending flange 83. The other end of the body 80A is closed by a conical end wall 84. Extending at an angle adjacent the end wall 84 is a discharge nozzle 85 having a discharge orifice. A displaceable piston 86 having a truncated conical shape complementing the internal configuration of the end wall 84 is provided to seal the opening 82.

As hereinbefore described, the external surface of the nozzle 85 adjacent the discharge end or orifice is coated with a layer of adhesive or bonding material to which minute fibers or flocking 87 is adhered to provide a brush like arrangement about the discharge end of the nozzle 85. The fibers or flocking 87 extend generally in a radially outwardly direction about the entire circumference of the nozzle 85, and in a longitudinally axially direction about the end surface defining the discharge orifice; e.g. as best noted in FIG. 9.

As described with respect to the previous embodiments, the brush like arrangement defined by the fibers or flocking 87 about the discharge end of the nozzle 85 enables a dentist to spread or burnish the material being dispensed by the capsule onto the surface of a tooth in a continuous and expedient manner not previously possible.

Figure 13:
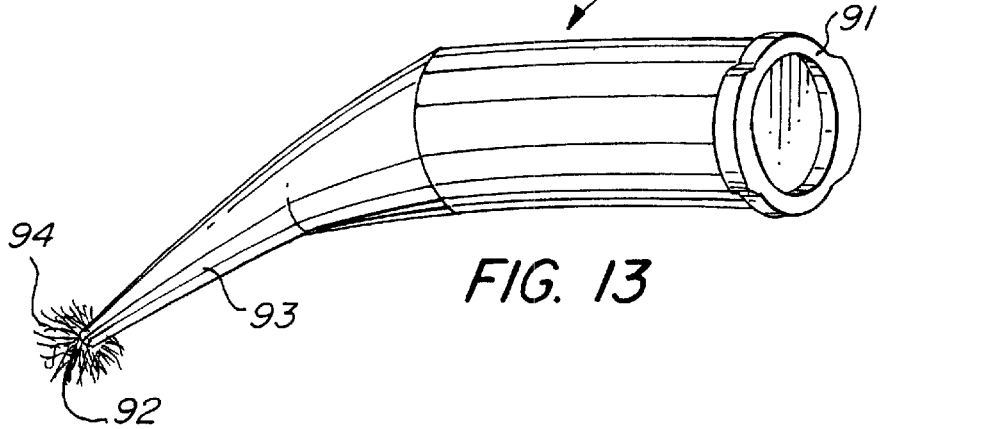
FIG. 13 is a perspective view of another form of the invention.

FIG. 13 illustrates another modified form of the invention. In this embodiment, the capsule 90 is similar to that of FIGS. 1 to 3, except that the flange 91 is formed as a Luhr locking flange similar to the flange 53 of FIG. 7. Also, the discharge end 92 of the discharge nozzle 93 may terminate in a spherical or ball shape as illustrated in FIG. 5, and minute fibers or flocking 94 is adhered to the spherical or ball end 92 as hereinbefore described with respect to FIGS. 4 to 6. In all other respects, the embodiment of FIG. 13 is similar to that of FIGS. 1 to 3.

Figure 14:
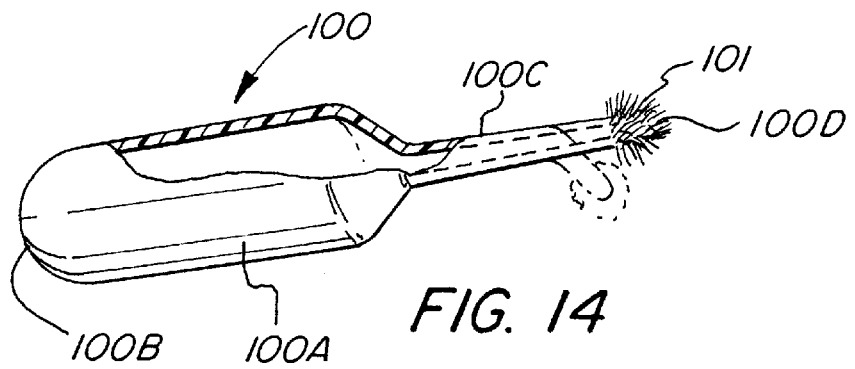
FIG. 14 is another modified form of the invention having parts broken away.

FIG. 14 is directed to another form of the invention. As shown, the embodiment of FIG. 14 is directed to a dental container applicator 100 having a hollow body portion 10A, which is closed at one end 100B and having its other end terminating in an elongated discharge nozzle 100C. The body of the applicator 100 is preferably formed of a flexible plastic material whereby the body portion 101A functions in the nature of a squeeze bottle. Disposed within the body portion 100A is a predetermined amount of fluent dental material.

In accordance with this invention, the discharge nozzle adjacent its orifice opening 100D is provided with a layer of suitable adhesive to which the minutes fibers or flocking 101, similar to that hereinbefore described, are adhered. To effect the discharge of the dental material disposed within the body portion 100A, the user need only squeeze or deflect the sides of the body portion 100A, causing the dental material to be expressed out from the nozzle 100C as may be required. Because of the flocking 101 forming an external brush element about the orifice opening 101D, the user or dentist is provided with a means to brush, burnish or spread the dental material onto the tooth as needed, as the material is being expressed.

From the foregoing, it will be apparent that various features of the respective embodiments can be interchanged with one another. For example, the flange circumscribing a particular embodiment may be formed with either an annular flange 30C as disclosed in FIG. 1 or a Luhr locking flange 53 or 91 as disclosed in FIGS. 7 or 9. Also, the discharge end of a given capsule or tip may be formed simply with a discharge orifice as in FIG. 1 or with a spherical or ball shape 44 as disclosed in FIG. 5. It will also be apparent that the configuration of the body portion of the capsule or tip may be variously shaped.

While the present invention has been described with respect to various embodiments, modifications and variations may be made without departing from the spirit or scope of this invention.

What is claimed is:

1. A dental container type applicator comprising:

a body portion, said body portion having a discharge nozzle connected to one end thereof, said discharge nozzle having a discharge orifice, and a plurality of minute fibers adhered to said discharge nozzle adjacent said discharge orifice, said fibers extending about the circumference of said discharge nozzle in the immediate vicinity of said discharge orifice by which the dental material being expressed can be spread, painted and burnished onto a tooth structure as the material is being expressed.

2. A dental container type applicator as defined in claim 1 wherein said discharge nozzle terminates a spherical shaped tip circumscribing said orifice, and said minute fibers being adhered to said spherical shaped tip and extending in a generally radially outwardly direction relative thereto.

3. A dental container type applicator as defined in claim 1 and including:

said body portion having a full open end opposite said discharge nozzle, a laterally outwardly extending flange circumscribing said full open end, and a displaceable piston sealing said full open end.

4. A dental container type applicator as defined in claim 3 wherein:

said flange comprises a Luhr locking flange.

5. A dental container type applicator as defined in claim 1 wherein said discharge nozzle comprises:

a needle like cannula connected to said body portion, said needle like cannula being formed of a ductile metal whereby said cannula can be readily bent so that the discharge orifice is disposed at an angle relative to the axis of said body portion, and said fibers being connected to said cannula in the vicinity of said discharge opening.

6. A dental container type applicator comprising:

a body portion formed of a suitable flexible material, said body portion being closed at one end thereof and defining a reservoir for containing a supply of fluid dental material, a discharge nozzle connected to the other end of said body portion, said discharge nozzle terminating in a discharge orifice, and a plurality of minute fibers adhered to said discharge nozzle in the vicinity of said discharge orifice, wherein said fibers project in a generally radially outward direction about the entire circumference of said discharge nozzle.

7. A dental container type applicator in the form of a dental tip comprising:

a body portion having an opening at one end, and a discharge nozzle connected to the other end of said body portion, a circumscribing flange disposed intermediate said body portion, and extending radially outwardly therefrom, said discharge nozzle terminating at a discharge orifice, and minute fibers projecting outwardly about the circumference of said discharge nozzle in vicinity of said discharge orifice.

8. A dental capsule comprising:

an elongated body portion defining a reservoir for containing a predetermined amount of fluid dental material, said body portion being closed at one end and having an opening at the other end thereof, a discharge nozzle disposed at an angle relative to the longitudinal axis of said body portion adjacent said closed end, said discharge nozzle being disposed in communication with said reservoir at one end having an end surface defining a discharge orifice at the other end thereof, a displaceable piston for sealing said open end of said body portion, an outwardly projecting flange circumscribing said open end, and a plurality of minute fibers adhered to said discharge nozzle externally thereof in the vicinity of said discharge orifice to provide unobstructed flow fluid through said discharge orifice.

9. A dental capsule comprising:

an elongated body portion defining a reservoir for containing a predetermined amount of fluid dental material, said body portion being closed at one end and having an opening at the other end thereof, a discharge nozzle disposed at an angle relative to the longitudinal axis of said body portion adjacent said closed end, said discharge nozzle being disposed in communication with said reservoir at one end having an end surface defining a discharge orifice at the other end thereof, a displaceable piston for sealing said open end of said body portion, an outwardly projecting flange circumscribing said open end, and a plurality of minute fibers adhered to said discharge nozzle in the vicinity of said discharge orifice, wherein said fibers are adhered to said discharge nozzle about the entire circumference thereof.

10. A dental capsule as defined in claim 9 wherein said fibers project generally in a radially outward direction about the outer circumference of said discharge nozzle, and in a generally axial direction relative to the end surface defining said discharge orifice.

11. A dental capsule comprising:

an elongated body portion defining a reservoir for containing a predetermined amount of fluid dental material, said body portion being closed at one end and having an opening at the other end thereof, a discharge nozzle disposed at an angle relative to the longitudinal axis of said body portion adjacent said closed end, said discharge nozzle being disposed in communication with said reservoir at one end having an end surface defining a discharge orifice at the other end thereof, a displaceable piston for sealing said open end of said body portion, an outwardly protecting flange circumscribing said open end, and a plurality of minute fibers adhered to said discharge nozzle in the vicinity of said discharge orifice, wherein said discharge nozzle having a tip end in the form of a sphere, and said fibers being adhered to the surface of said sphere.

12. A dental container type applicator comprising:

a body portion for containing a supply of dental material, a discharge nozzle terminating in a discharge orifice connected to said body portion, and minute fibers connected to the external surface of said discharge nozzle in the vicinity of said discharge orifice by which the dental material being expressed can be spread, painted or burnished onto a tooth structure without-obstructing the flow of material as it is being expressed.

* * * * *